United States Patent [19]

Duret et al.

[11] Patent Number: 4,742,464
[45] Date of Patent: * May 3, 1988

[54] METHOD OF MAKING A PROSTHESIS, ESPECIALLY A DENTAL PROSTHESIS

[76] Inventors: Francois Duret, Rue Paul Claudel, Le Grand Lemps (Isere); Christian Termoz, 2, Place Victor Hugo, Grenoble (Isere), both of France

[*] Notice: The portion of the term of this patent subsequent to Sep. 9, 2003 has been disclaimed.

[21] Appl. No.: 903,595

[22] Filed: Sep. 3, 1986

Related U.S. Application Data

[60] Division of Ser. No. 673,655, Nov. 21, 1984, Pat. No. 4,663,720, which is a continuation-in-part of Ser. No. 580,776, Feb. 21, 1984, abandoned, which is a continuation of Ser. No. 262,905, May 12, 1981, abandoned, which is a continuation-in-part of Ser. No. 485,059, Apr. 14, 1983, Pat. No. 4,611,288.

[51] Int. Cl.$^4$ .......................... G06F 15/00; A61C 9/00
[52] U.S. Cl. ...................................... 364/474; 433/214
[58] Field of Search ................ 364/474, 475, 168; 356/347, 357, 358; 433/204, 213, 214, 223, 55, 68, 73

[56] References Cited

U.S. PATENT DOCUMENTS

| | | | |
|---|---|---|---|
| 3,749,493 | 7/1973 | Macouski | 356/357 |
| 3,943,278 | 3/1976 | Ramsey | 356/357 |
| 4,324,546 | 4/1982 | Yamada | 433/213 |
| 4,385,360 | 5/1983 | Heitlinger | 364/475 |
| 4,411,626 | 11/1983 | Becker | 364/168 |
| 4,464,052 | 8/1984 | Newman | 356/347 |
| 4,575,805 | 3/1986 | Moermann | 364/475 |

FOREIGN PATENT DOCUMENTS

| | | | |
|---|---|---|---|
| 0040165 | 11/1981 | European Pat. Off. | 433/214 |
| 0091876 | 10/1983 | European Pat. Off. | 433/214 |

OTHER PUBLICATIONS

Translation of EP 40165.
Translation of EP 91876.

*Primary Examiner*—Jerry Smith
*Assistant Examiner*—Allen MacDonald
*Attorney, Agent, or Firm*—Karl F. Ross; Herbert Dubno

[57] ABSTRACT

A method of making a dental prosthesis in which data representing standard tooth shapes and sizes, relationships between teeth and adjacent and occlusive teeth and characteristics for securing a prosthesis to a prepared site, and machining instructions for shaping a blank to the configuration of a dental prosthesis for direct implantation are stored in a computer memory. After preparing a site in the mouth of a patient to receive a dental prosthesis, the dental surgeon projects optically a grating upon said site in the mouth of the patient and generates an interference pattern representing a holistic impression of said site and its relationship to adjacent structures. The interference pattern is converted into data along x,y,z coordinates in a cartesian coordinate system representing machining of a blank to fit said site and matching data obtained by comparing the impression with the computer standards are used to select a best-fit shape and size. A machine tool is numerically controlled with the x,y,z coordinate data and x,y,z coordinate data from the match made by the computer and representing the shape and size of the prosthesis to totally and three-dimensionally fabricate said prosthesis in said machine tool.

5 Claims, 8 Drawing Sheets

| | | | |
|---|---|---|---|
| POINT NUMÉRO 1 | X = 1.43 286 | Y = 0.08 771 | Z = − 0.32 480 |
| POINT NUMÉRO 2 | X = 1.47 239 | Y = − 0.03 849 | Z = − 0.32 482 |
| POINT NUMÉRO 3 | X = 1.54 664 | Y = − 0.14 066 | Z = − 0.32 481 |
| POINT NUMÉRO 4 | X = 1.64 496 | Y = − 0.20 727 | Z = − 0.32 480 |
| POINT NUMÉRO 5 | X = 1.75 752 | Y = − 0.23 679 | Z = − 0.32 480 |
| POINT NUMÉRO 6 | X = 1.87 423 | Y = − 0.23 033 | Z = − 0.32 480 |
| POINT NUMÉRO 7 | X = 1.98 552 | Y = − 0.19 006 | Z = − 0.32 480 |
| POINT NUMÉRO 8 | X = 2.08 213 | Y = − 0.11 948 | Z = − 0.32 480 |
| POINT NUMÉRO 9 | X = 2.15 522 | Y = − 0.02 340 | Z = − 0.32 480 |
| POINT NUMÉRO 10 | X = 2.19 637 | Y = 0.09 211 | Z = − 0.32 481 |
| POINT NUMÉRO 11 | X = 2.19 768 | Y = 0.21 962 | Z = − 0.32 481 |
| POINT NUMÉRO 12 | X = 2.15 205 | Y = 0.35 027 | Z = − 0.32 482 |
| POINT NUMÉRO 13 | X = 2.04 011 | Y = 0.50 696 | Z = − 0.32 480 |
| POINT NUMÉRO 14 | X = 1.92 823 | Y = 0.61 991 | Z = − 0.32 480 |
| POINT NUMÉRO 15 | X = 1.82 272 | Y = 0.68 935 | Z = − 0.32 482 |
| POINT NUMÉRO 16 | X = 1.72 603 | Y = 0.72 258 | Z = − 0.32 481 |
| POINT NUMÉRO 17 | X = 1.63 922 | Y = 0.72 591 | Z = − 0.32 480 |
| POINT NUMÉRO 18 | X = 1.56 338 | Y = 0.70 243 | Z = − 0.32 480 |
| POINT NUMÉRO 19 | X = 1.50 010 | Y = 0.65 231 | Z = − 0.32 480 |
| POINT NUMÉRO 20 | X = 1.45 169 | Y = 0.57 233 | Z = − 0.32 480 |
| POINT NUMÉRO 21 | X = 1.42 147 | Y = 0.45 562 | Z = − 0.32 482 |
| POINT NUMÉRO 22 | X = 1.41 385 | Y = 0.29549 | Z = − 0.32 480 |

FIG.18

FIG.19

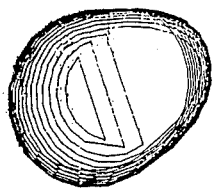

FIG.20

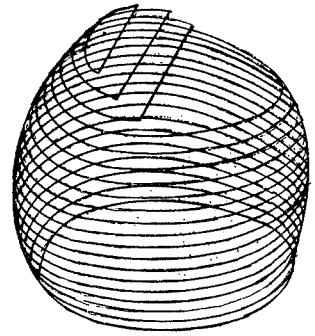

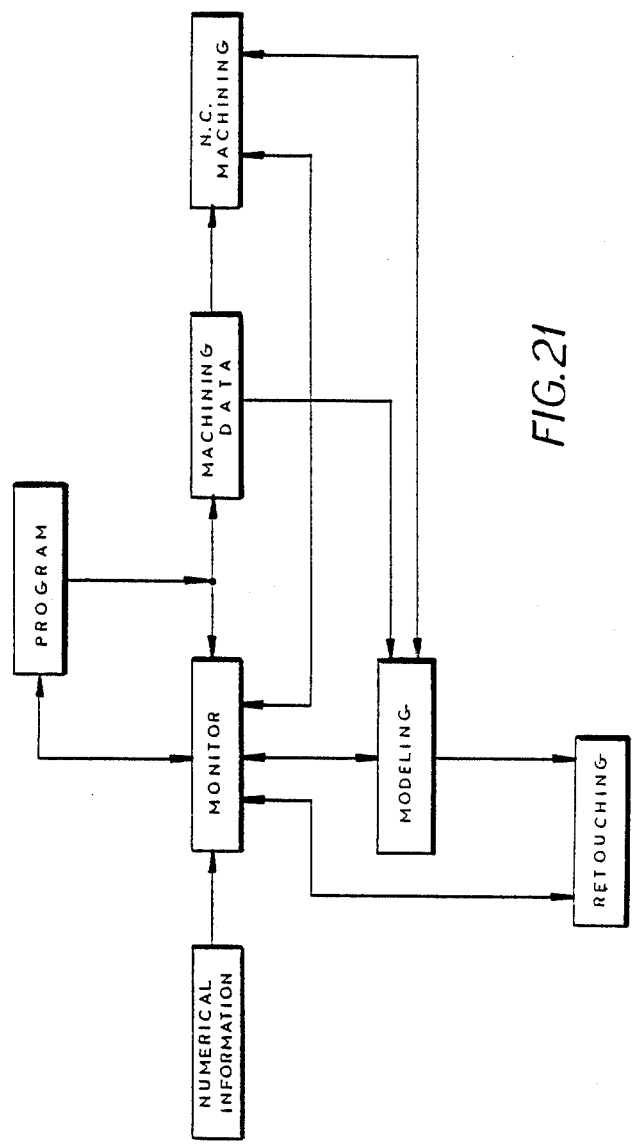

METHOD OF MAKING A PROSTHESIS, ESPECIALLY A DENTAL PROSTHESIS

CROSS REFERENCE TO RELATED APPLICATIONS

This application is a division of Ser. No. 06/673,655 filed Nov. 1984 (now U.S. Pat. No. 4,663,720) as a continuation-in-part of Ser. No. 06/580,776 filed Feb. 21, 1984 (now abandoned) which is a continuation of Ser. No. 06/262,905 filed May 12, 1981 (now abandoned) and is also a continuation-in-part of copending application Ser. No. 06/685,509 filed Apr. 14, 1983 (now U.S. Pat. No. 4,611,288).

FIELD OF THE INVENTION

Our present invention relates to a method of and to an apparatus for the making of a prosthesis and especially a dental prosthesis. More particularly, this invention relates to a system for making a dental prosthesis in which, after preparation of the site in the mouth, the dental practitioner need only develop an electronic impression of this site as the sole intervention step before inserting the completed prosthesis.

BACKGROUND OF THE INVENTION

The aforementioned application points out that earlier methods of making dental prostheses, e.g. crowns, plates and replacement teeth, involved a multiplicity of steps, many of which required intervention in the mouth of the patient.

Not only was the patient required to attend the dental practitioner a comparatively large number of times but frequently the intervention was painful, especially during the fitting stages.

In the formation of a dental crown, for example, the operations include the grinding of the tooth to be replaced in order to obtain a truncated stump, the taking of an impression of the stump using an elastomeric path in order to obtain a mold whose hollow part has a shape which is complementary to that of the stump, the casting of plaster into said mold in order to obtain a reproduction of the stump, the preparation of the crown in wax taking into consideration adjacent and antagonistic teeth (a process which was generally highly subjective and the effect of which required high skill and long years of experience by the practitioner), the positioning of the crown in a coating cylinder, the melting out of the wax, the injection of molten metal to replace the wax, stripping and polishing of the metal crown, and, setting of the crown on the stump.

In spite of the fact that these numerous operations were carried out by highly skilled and fastidious dental surgeons, frequently modification of the prosthesis was required after the formation.

Indeed, because of the large number of steps which were involved and the fact that even with mechanical impressions, accurate fits could not be ensured, and because the relationship of each prosthesis to the adjacent and antagonistic teeth was something which had to be gauged subjectively by the practitioner, the production of a dental prosthesis hitherto seldom could be accomplished without the many visits mentioned previously. Indeed, in spite of numerous fitting operations, there was always the danger that the finished prosthesis would cause discomfort to the patient.

Another disadvantage of the earlier systems should also be apparent. For example, the metals used had to be fluid or malleable at easily obtainable temperatures. The numerous steps required the intervention of a laboratory and skilled practitioners at different stages in addition to the dental surgeon. The equipment required overall, including an oven, sand-blasting machine, inserting equipment, contributed substantially to the cost of producing the prosthesis.

Because the temperature to which the materials were subjected, ranged from room temperature at which some work was done to the casting temperature, to the body temperature of the patient, uncontrolled thermal expansion posed a problem.

In the production of other prosthesis, it was necessary to utilize a so-called "bloody impression" when, for example, an impression was required from injured bone. This involved pain and required especially sterile surgical procedures and handling of the impression media. Obviously, repeated fits here were an even more severe drawback.

OBJECTS OF THE INVENTION

It is, therefore, a principal object of the present invention to provide an improved method of and apparatus for the production of a prosthesis, and especially a dental prosthesis, whereby the numerous interventions with respect to the body of the patient can be eliminated and indeed many, if not all, of the drawbacks of the earlier systems described can be obviated.

Another object of this invention is to provide a method and apparatus for the fabrication of a dental prosthesis which allows the fabrication of the entire prosthesis or at least a substantial portion thereof by a machining operation outside the mouth of the patient so that the disadvantages of casting techniques are obviated.

Still another object of this invention is to provide a method and apparatus which extends the principles set forth in the above mentioned copending application.

SUMMARY OF THE INVENTION

These objects and others which will become apparent hereinafter are attained, in accordance with the invention, in a method whereby an optical impression is taken of the prosthesis site in the mouth and provides an interferogram image of the region at which the prosthesis is to be positioned and its relationship with adjoining teeth and occlusive teeth so that this image can be quantified in terms enabling selection from a stored collection of tooth shapes and sizes in a best-fit approach.

According to the invention, utilizing the data obtained from the best-fit approach, i.e. from the stored data regarding the standard shape and the modifications required to conform the best-fit shape to the tangent place and occlusive conditions from the particular site, a blank is machined by a numerically controlled three-dimensional machine tool so that both the fit to the location and the relationship of the machined prosthesis to the adjoining structures are optimum and determined exclusively by the optical impression.

We have found that, utilizing a computer programmed for computer assisted design of three-dimensional objects to which the optical impression input is fed, and a machine tool of a numerically controlled type which is numerically controlled by this computer, a highly compact apparatus can be provided which allows the dental practitioner to carry out the computer fabrication operation at his office after seeing the patient only once for preparation of the site and the optical impression so that on the next visit the completed prosthesis may be applied. Indeed, since the entire operation takes only a short period of time, a completed prosthesis may be provided while the patient waits.

While we have used the term "interferogram" to refer to the image received, this expression is used in its broadest sense to refer to the obtention of a three-dimensional or holistic image. The preferred mode of obtaining this image is by interferometry which will be discussed below, although laser holographic techniques may be used as well or in addition.

Consequently, the method of the invention takes an optical impression of that part of the body which is designed to receive the prosthesis, effects a numerical, analog, and, electric clock conversion of the impression into data which is processed taking into account the characteristics of the prosthesis to be obtained and in determining the shape of the latter and sculpturing the prosthesis three-dimensionally with a numerically controlled machine tool.

The process of the invention provides for completely automatic production of a prosthesis with the possibility of preserving with great accuracy the optical impression in all of its holistic aspects. Although the process requires relatively sophisticated and costly apparatus, since it requires a computer and a numerically controlled machine tool, it has the advantage of high precision in the production of the prosthesis and high speed production thereof because it eliminates all of the intermediate phases of earlier techniques.

By eliminating these intermediate phases and the equipment involved in them and because of the gain in time, the cost of the apparatus of the invention is readily amortized, especially since the computer, which is required for the process, can also be used for other purposes.

As noted, an interferogrammatic impression is taken and advantageously two wave sources can be used, namely, an object beam diffracted by the object (the prosthesis site) and a refracted reference beam to obtain the impression in the form of wave interference patterns which can be evaluated and broken down into increments forming the numerical or digital data processed by the computer.

Since the wave interference pattern carries in itself the notion of distance, a holistic image makes it possible to obtain an impression that will not be deformed and will remain intact when carried over via the computer to the machine tool.

In accordance with a first possibility, the interference pattern is generated on a holographic plate while in another possibility the patterns or information are scanned directly utilizing a numerical, analog or electric analog converter.

The impression can advantageously be obtained by projection onto the organ or site to be provided with the prosthesis of a perfectly monochromatic laser wave which does not traumatize the tissue having a power, for example of 100 millijoule. Preferably an interference grating pattern can be projected and this need not use a coherent light source.

The impression can be taken on visible or exposed organs such as two stumps when the prosthesis is a dental crown or even through some media such as the skin or body tissues in order to obtain the impression of subjected organs for osteosynthesis prosthesis without the need for bloody impression techniques.

In a preferred mode of operation, the computer is preprogrammed to contain in memory detailed information regarding the possible prosthesis to be manufactured. This can include information regarding the shape of the prosthesis, e.g. standard tooth shapes, information relating to relationships of the prosthesis to adjacent and antagonistic structures (e.g. information regarding an adjoining tooth and antagonistic tooth) and even information regarding the details of attachment of the prosthesis to the implanation site (e.g. adhesive clearances).

The three-dimensional impression of the site is then automatically quantified in the manner described and stored in the computer which can call up the stored data regarding the location, standard tooth shapes and sizes and the like enabling the best-fit of the tooth or teeth to that locus.

The teeth can be displayed on a screen of a video monitor or CRT associated with the computer to allow selection by the dental practitioner. After the selection is made from the stored data regarding the selection, the tooth sizes may be modified in view of the occlusive place and the adjacent structures automatically in accordance with preprogrammed information in the computer and the result is completed with the data of the stump and the site to enable an information set to be provided to the machine tool for the precise three-dimensional sculpturing of the finished prosthesis from a material as assisted by the operator.

The invention will be further described with reference to the manufacture of a dental crown. This is to be considered a preferred, but by no means exclusive embodiment.

In accordance with the invention, data roughly describing a plurality of standard teeth is stored in a computer. Data of at least 32 adult teeth, 20 baby teeth and possibly some other teeth of special shape must be stored.

Next, an optical image of the implantation site of the prosthesis is obtained. Specifically, the image is obtained by first projecting a luminous grating onto the implantation site.

The grating deforms in accordance with the shape of the site. Interference patterns are then created between the so-deformed grating and a reference grating.

The interference between the two gratings results in the appearance of interference fringes. Interference patterns consisting of the fringes are subjected to analog-digital conversion and the resulting values are stored in the computer. The computer then controls a machine tool which manufactures the prosthesis without any further need to inconvenience the patient and, further, without any need for manual intervention by the doctor or dentist concerned.

BRIEF DESCRIPTION OF THE DRAWING

The above and, other objects, features and advantages will become more readily apparent from the following description reference being made to the accompanying drawing in which:

FIGS. 18, 19 and 20 illustrate the machining of successive planes under program control; and FIG. 21 is a function diagram for the apparatus of FIG. 7.

SPECIFIC DESCRIPTION

The present invention will be discussed with regard to the manufacture of a crown for a tooth. It should be noted that the invention can be equally used for other types of prosthetic devices such as osteosynthetic. It must further be noted that understanding of the invention, though not operation of the resulting equipment, requires a person skilled in the art of Computer Aided Design and Manufacture (CAD/CAM). Specifically, skill in the utilization of commercially available CAD/CAM equipment is essential.

Setting up the computer so that the method of the present invention may be used, in the case of a dental prosthesis involves the insertion into memory of data roughly defining 32 adult teeth, 20 baby teeth and, as required, additional teeth having odd shapes.

The data defining the shape of each of the above-mentioned teeth is entered into the memory of the computer in numerical form. Each tooth is defined by x, y, z coordinates of a plurality of points, as well as by a number of reference values, such as the center of gravity, and lines, circles or surfaces which may be mathematically defined. A computer aided design system (CAD) suitable for this purpose is, for example, the "EUCLID AND VAX" (Geometric Construction), CAD, of the Digital Equipment Corp.

It should be noted that this entry into memory of rough or standard tooth shapes is a one time operation and need not be repeated for each patient.

After the dentist has prepared the site of implantation of the prosthesis in the conventional manner, he proceeds to project a luminous grating onto the implantation site with either coherent or non-coherent light. The grating deforms in dependence on the shape of the site, so that interference fringes are created between the so-deformed grating and a reference grating which is not deformed.

FIGS. 1-4 are examples of so-created patterns. The interference patterns illustrated in FIGS. 1-4 correspond to four optical recordings of four faces of a tooth.

Reading out of the images may take place after recording on a holographic plate or other suitable recording medium or, preferably, directly by a television camera or a plasma display.

Figure 1:
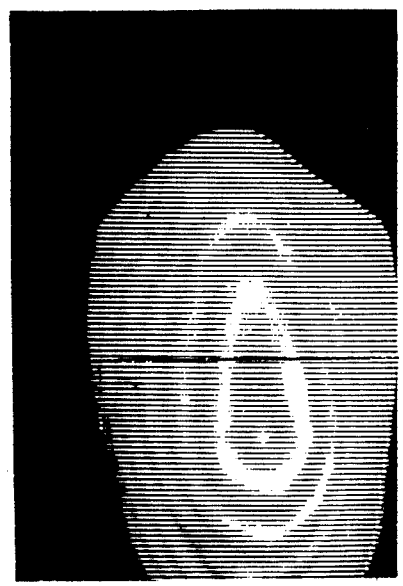
FIGS. 1-4 are interference patterns of four surfaces of one tooth.
Figure 2:
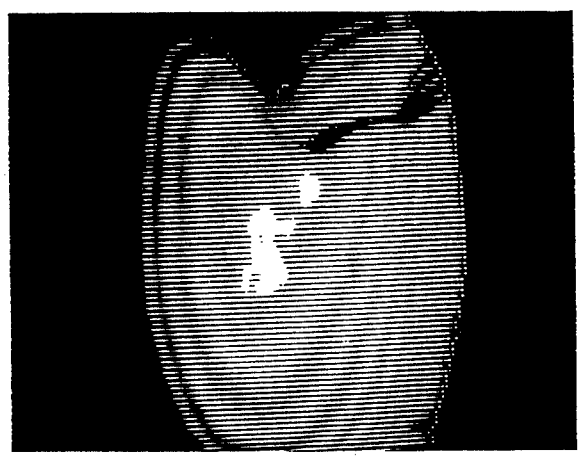
Figure 3:
Figure 4:
Figure 5:
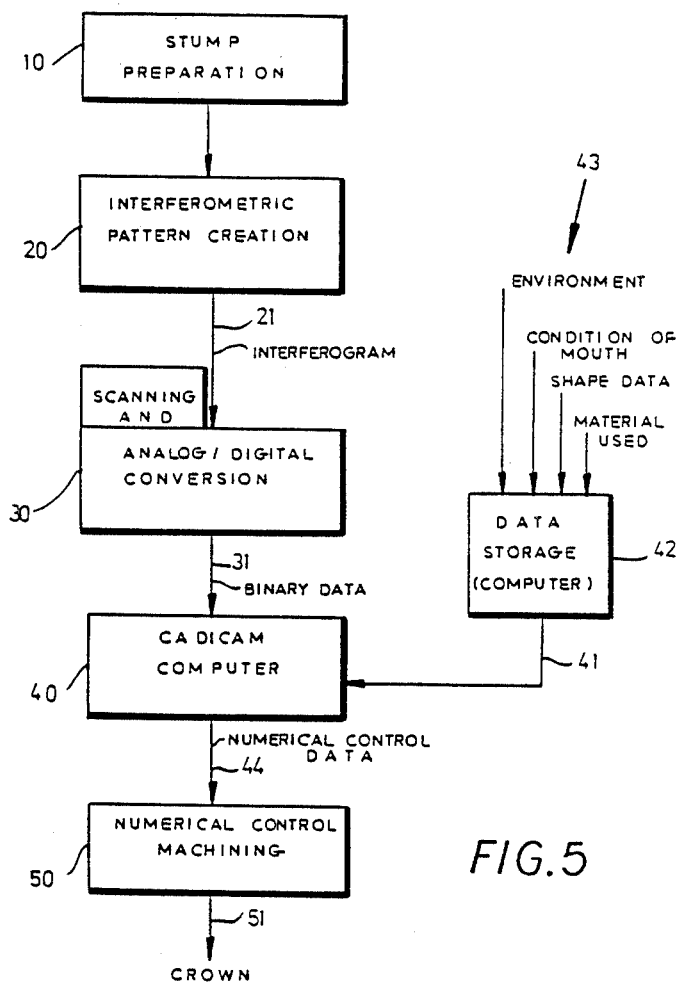
FIG. 5 is a block diagram of the system of the present invention.
Figure 6:
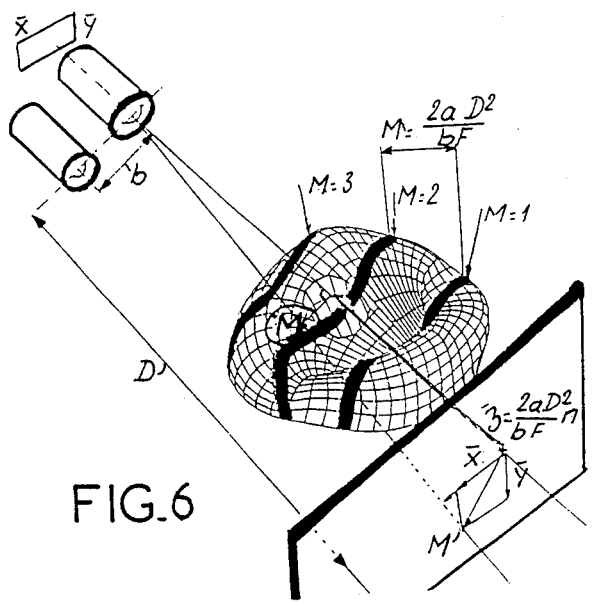
FIG. 6 is a schematic diagram illustrating the apparatus for creating interference patterns of a tooth.

This is illustrated generally by steps 20 and 30 in FIG. 5. FIG. 6 illustrates a light source, 101, projecting a grating onto the tooth site. The grating is correspondingly deformed and an interference pattern, 102, created by superimposition of an undeformed reference grating.

The pattern is scanned by a TV camera 103. Plane 104 represents an interference plane. The pickup can be in a video camera or a CCD (chargecoupled device) camera.

Figure 7:
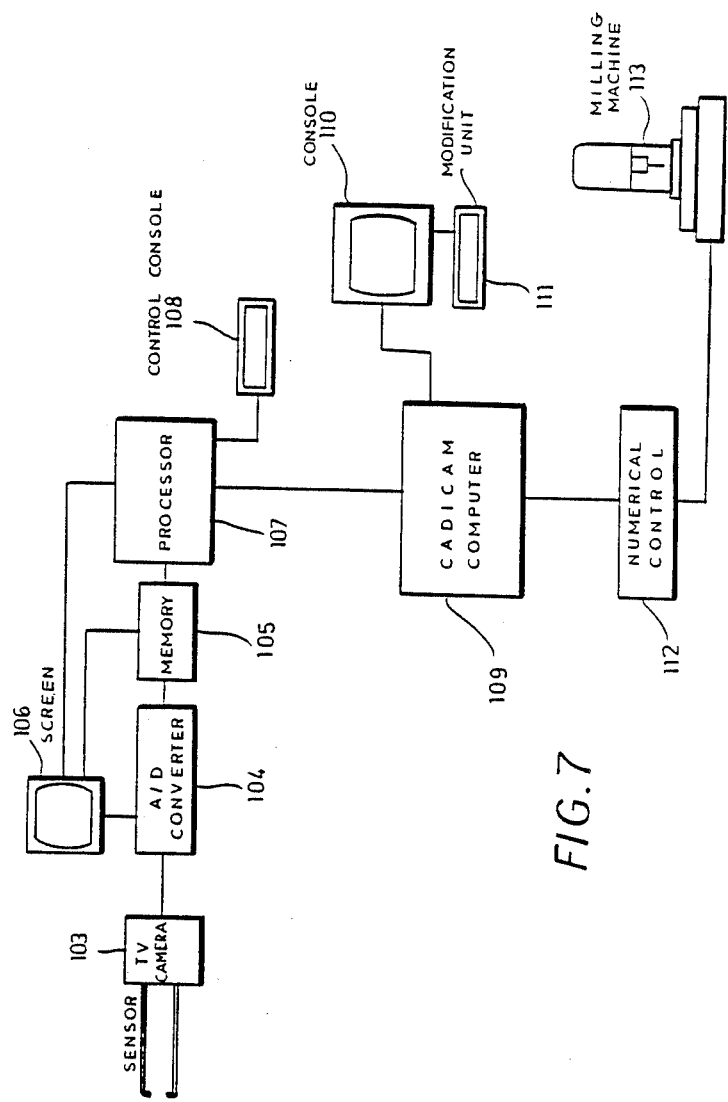
FIG. 7 is a block diagram of the apparatus linking the interference pattern readout to the machine tool apparatus.

The equipment linking the camera sensor to the final machine tool, for example a milling machine, is illustrated in FIG. 7. A television camera 103 scans the interference pattern. An analog/digital converter 104 converts the scanned data and stores it in memory. The image is also projected onto a cathode ray screen 106. The image on the screen is subjected to processing for purposes of simplification, as will be explained in greater detail below. For this purpose, the operator controls a control console 108 which, in turn, controls an image processor 107. After the image has been processed, it is subjected to computer-aided design in a computer 109, also to be described in greater detail below. The output of computer 109 is displayed on a suitable screen 110, the image on which may be modified by operation of a modification unit 111. The final output of the computer is numerical control data which, through a numerical control unit 112 controls the final machine tool, here a micro-milling machine 113 (see also FIG. 21). Processing of the interference patterns proceeds as follows:

The interference patterns have certain contour lines which are a function of the volume of the tooth.

For any point, the xy coordinates are obtained by direct read-out. The third coordinate, z, can easily be calculated with the aid of a formula giving the distance h between two interference fringes;

$$h = 2aD^2/bF$$

As illustrated in FIG. 5:

F is the focal distance;
b is the distance between the transmitting and receiving objectives;
a is the spacing between grating lines;
and D is the distance between the apparatus and the interference plane.

The third coordinate z is given by the formula
$$a = (2aD^2/bF)n$$

where n represents the number of fringes.

Before the proceeding to determine the different coordinates of each point, the image is reduced to a skeletal version so that the number of reference values of z is the least possible. This is accomplished by reducing the number of points in each curve and reducing the number of curves, keeping in mind the minimum degree of accuracy which must be preserved.

Preferably, the coordinates of each point are obtained using FORTRAN, for example FORTRAN 22, by which, for each value of z, the corresponding values of x and y are found.

The analog/digital conversion of the data takes place very simply by counting of fringes or by sinusoidal interpolation between fringes. It is considered that a fringe is black and that the space between fringes is white. After the simplification, each fringe corresponds to a black line of several microns. The value 0 is assigned to each black point, while the value 1 is applied to each white point. The formula mentioned above then can be used to determine the value of z correctly. The values of x and y are given by the position of the point being analyzed on the image plane.

All these operations are carried out by the computer which, for this purpose, is equipped especially with commercially available programs such as VAX730 of the Digital Equipment Corporation or with booting or operating cards such as Thompson CSF (31138 ANTI-BLOWING) and associated Program (THX 5002: Frequency Generator and Command Logic, and THX 5003: Video channel and analog digital conversion).

Figure 8:
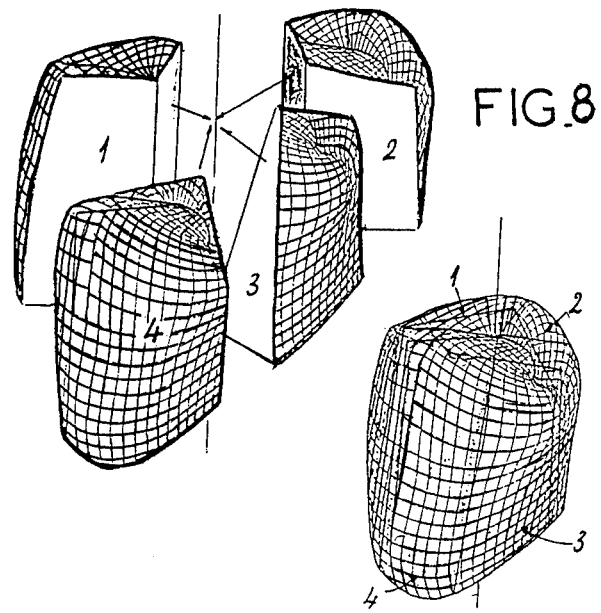
FIG. 8 illustrates the combination of a plurality of views to create a three-dimensional model by CAD (computer assisted design)

To the extent that the implantation site and the adjacent areas of the prosthesis necessitate views from different angles, the computer will reconstitute the overall shape of the site by combining such views as is illustrated in FIG. 8. This figure was obtained by the Euclid and Vax, FUSION design package.

Next, the determination of the volume (envelope) of the prosthesis must be carried out.

This is a two-step operation.

Figure 9:
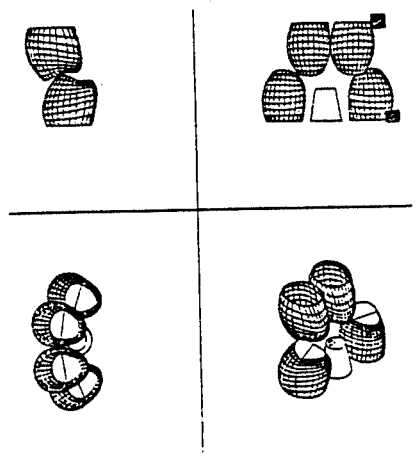
FIG. 9 illustrates four views of the implantation zone of the prosthesis.

(a) imaging of the implantation zone of the prosthesis; (FIG. 9 shows this zone from four angles);

(b) adaptation of the standard form or rough outline of the tooth stored in the computer memory to the visualized shape of the prosthesis.

Figure 10:
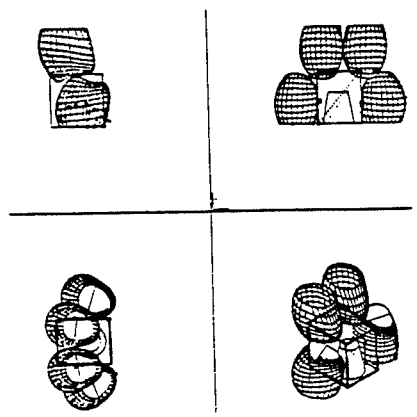
FIG. 10 illustrates the actual planes limiting the volume into which the prosthesis must be inserted.

First, the operator causes an area to appear on a cathode ray screen into which the standard form of a theoretical tooth in the memory is inserted. This volume is parallelipiped and is obtained by geometric determination of 6 planes, taking into consideration the contact zones with the neighboring teeth (planes 1 and 2), the front and rear faces of the neighboring teeth (planes 3 and 4) the contacting surface of the opposite teeth (plane 5) and finally the lower limit of the implantation zone of the prosthesis (plane 6). This defines the real limits of the volume into which the prosthesis must be inserted (FIG. 10).

To avoid having to enter excessive data into the computer, the prosthesis is generated by adaptation of a standard tooth shape in the computer memory to fit into this volume.

Figure 11:
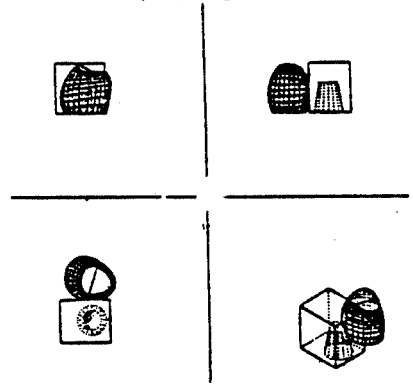
FIG. 11 illustrates the fitting of a standard tooth derived from computer memory into the volumetric space of the prosthesis.
Figure 12:
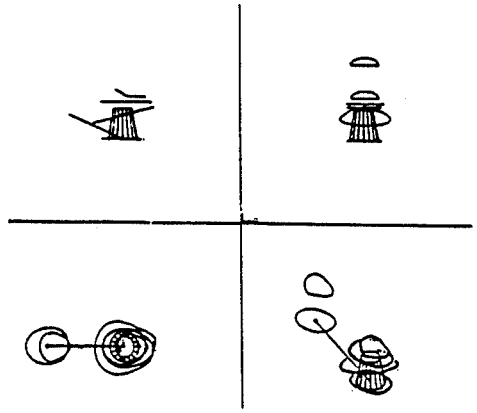
FIG. 12 illustrates movement of the center of gravity of the standard tooth onto the center of gravity of the implantation zone.
Figure 13:
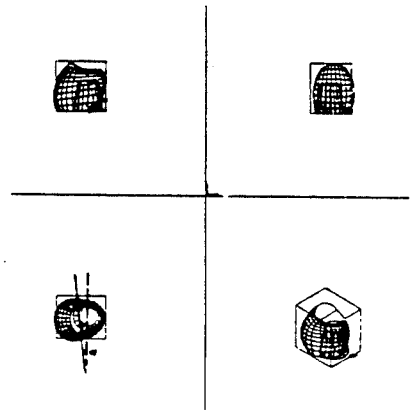
FIG. 13 illustrates deformation of the external surfaces of the standard tooth to fit into the volume of the prosthesis.

As mentioned above, the operator first causes the theoretical tooth stored in the memory which is closest to the tooth to be fitted to appear on the screen (FIG. 11). By using a CAD/CAM package (Euclid: Geometric Transformation), and by controlling the cathode ray tube, the operator matches the form of the theoretical tooth to the previously determined volume or envelope. This adaptation is first made by moving the center of gravity of the standard tooth onto the center of gravity of the implantation site of the prosthesis (FIG. 12), then by deformation of the surfaces of the outline of the standard tooth, so that they are tangent to the planes limiting the volume of the previously determined envelope (FIG. 13).

Figure 14:
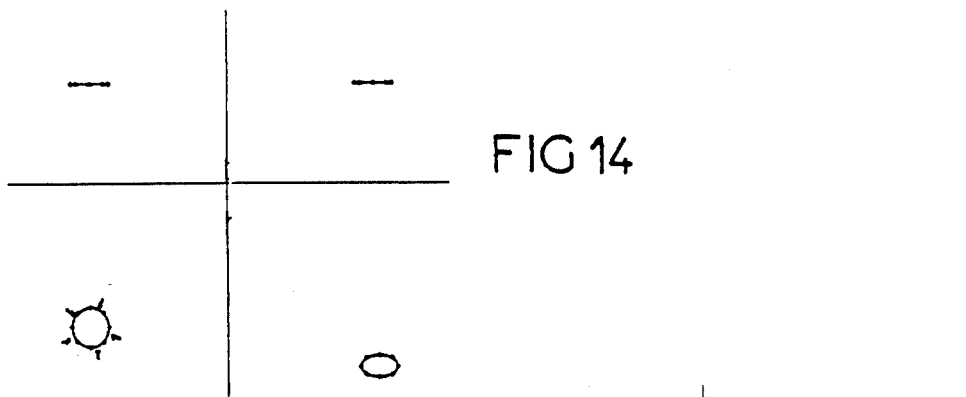
FIG. 14 illustrates the cement film on which the prosthesis is to be held.
Figure 15:
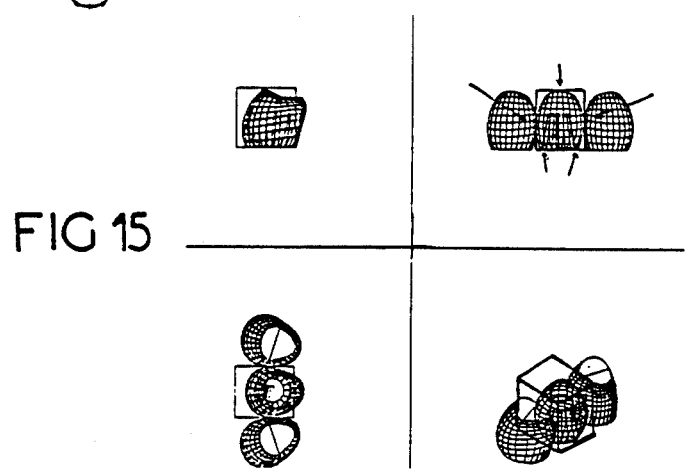
FIG. 15 illustrates the superposition of the bottom plane of the modified standard tooth with the corresponding plane of the implantation site.

The exterior surface of the prosthesis has thus been defined. The interior (lower) surface corresponds to that of the implantation site. The logic package (Euclid) then determines the actual volume of the prosthesis, taking into consideration the exterior surface previously defined, the shape of the implantation site, and finally, other factors such as the thickness of the cement film which will hold the prosthesis (FIG. 14). The combination of interior and exterior surfaces is effected by superposition of the implantation site on the lower limit of the standard tooth, as modified (FIG. 15).

Figure 16:
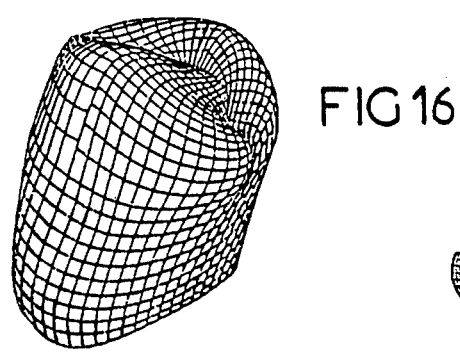
FIG. 16 illustrates the actual model of the prosthesis which has been derived from the standard model stored in the computers.
Figure 17:
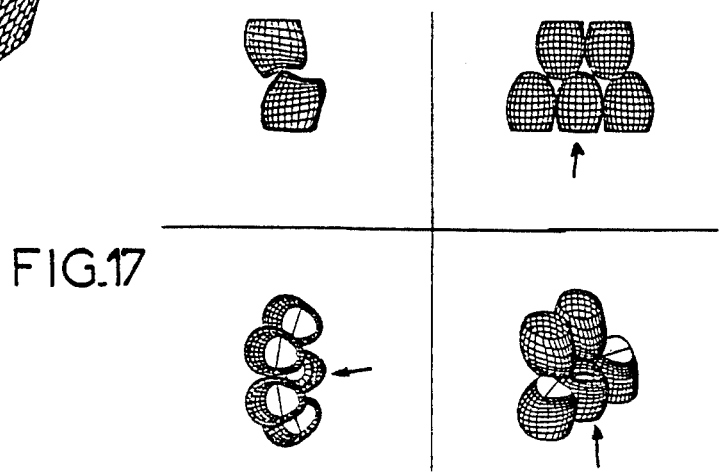
FIG. 17 shows four views of the final prosthesis in place.

The computer aided design system, such as Euclid and VAX, allows the transformation of the theoretical model into the actual model (FIG. 16). The results can be visualized according to predetermined views (FIG. 17). At this stage, visualization of the actual model of the prosthesis and its adjoining areas make it possible to verify the exact shape of the model and, if necessary, make modifications at particular points.

After the real model has thusly been determined, the CAD/CAM system controls the manufacture of the prosthesis or, depending upon the material utilized, of a casting into which the material for the prosthesis will be poured. FIG. 18 illustrates the program for manufacturing control of successive planes, as generated by Euclid. (FIGS. 19 and 20).

The process of the present invention thus has several principal stages which may be summarized as follows:

(a) one time creation of an optical pattern independently of the object itself and connected only to an interference phenomenon, either optical-optical or optical-electronic;

(b) immediate carrying out of an analog-digital conversion;

(c) determining the external and internal shape of the prosthesis solely by mathematical means within the computer, on the basis of CAD/CAM techniques, the computer having stored data defining standard shapes, such as the shape of the adult and baby teeth, which may be modified in accordance with the interference patterns derived from the particular patient.

It must be noted that nowhere in the process of the present invention is wax or resin used to make an imprint nor is there any manual adjustment of the prosthesis.

The process has been carried out successfully by the inventors to manufacture a prototype which functions perfectly and which allowed a dental prosthesis to be manufactured within 20 minutes.

It must of course be understood that, in particular, the process of the present invention makes use of a truly interferometric method. In a preferred embodiment, the interference patterns are not obtained by interference of a reference beam and a diffraction beam, but by interference between a grating which is not deformed and a luminous grating which is deformed by the zone being analyzed. It should be noted that it is not measurements of an object, but solely interference phenomena derived from the object which are utilized in the automatic manufacture of the prosthesis.

This interferometric method allows analog-digital conversion with the restricted financial means available in a, for example, dental office. The shape of the prosthesis is then derived strictly mathematically by a CAD/CAM system.

Further, the interferometric method allows the optical interference patterns to be obtained in a very short time, namely several microseconds (scanning at 5

MHz), data processing taking place in several seconds, as opposed to other methods which require either a long readout time for a short data processing time or a short readout time but a long processing time (30 minutes to an hour) with very powerful computers which are not financially within the reach of, for example, a dental office.

We claim:

1. A method of producing a prosthesis of an organ at a determined organ site, comprising the steps of:
    creating an interference pattern containing site data corresponding to a three-dimensional view of said organ site;
    scanning said interference pattern to produce digital site data;
    processing said digital site data to create machine tool data; and
    machining said prosthesis to fit said organ site directly under control of said machine tool data.

2. The method as set forth in claim 1, wherein said step of creating said interference pattern comprises the steps of projecting a laser beam onto said organ site, thereby creating an object beam diffracted in accordance with said site, and projecting an undiffracted resonance beam to interfere with said object beam, thereby creating said interference pattern.

3. A method as set forth in claim 2, further comprising the step of recording the so-created interference pattern;
    and wherein scanning said interference pattern comprises scanning a holograph.

4. A method as set forth in claim 1, wherein said creating an interference pattern comprises projecting a grating onto said organ site, thereby creating a deformed grating, and combining said deformed grating with an underformed grating, thereby creating said interference pattern.

5. A method as set forth in claim 4, wherein scanning said interference pattern comprises scanning said pattern directly with a television camera.

* * * * *